United States Patent
Zhang et al.

(10) Patent No.: US 11,213,555 B2
(45) Date of Patent: Jan. 4, 2022

(54) INTRAVENOUS INJECTION FOR ENHANCING IMMUNE FUNCTION

(71) Applicants: WEIFANG HUAYING BIOTECHNOLOGY CO., LTD., Weifang (CN); SHANDONG AGRICULTURAL UNIVERSITY, Tai'an (CN)

(72) Inventors: Yong Zhang, Weifang (CN); Youfei Shi, Tai'an (CN)

(73) Assignees: WEIFANG HUAYING BIOTECHNOLOGY CO., LTD., Weifang (CN); SHANDONG AGRICULTURAL UNIVERSITY, Tai'an (CN)

( * ) Notice: Subject to any disclaimer, the term of this patent is extended or adjusted under 35 U.S.C. 154(b) by 206 days.

(21) Appl. No.: 16/331,590

(22) PCT Filed: Sep. 8, 2016

(86) PCT No.: PCT/CN2016/098444
§ 371 (c)(1),
(2) Date: Mar. 8, 2019

(87) PCT Pub. No.: WO2018/045534
PCT Pub. Date: Mar. 15, 2018

(65) Prior Publication Data
US 2021/0023146 A1    Jan. 28, 2021

(51) Int. Cl.
A61K 9/00      (2006.01)
A61K 35/747    (2015.01)
A61K 35/745    (2015.01)
A61P 37/04     (2006.01)

(52) U.S. Cl.
CPC .......... *A61K 35/745* (2013.01); *A61K 9/0019* (2013.01); *A61K 35/747* (2013.01); *A61P 37/04* (2018.01)

(58) Field of Classification Search
None
See application file for complete search history.

(56) References Cited

U.S. PATENT DOCUMENTS

2014/0288159 A1   9/2014   Schrezenmeir
2015/0225692 A1   8/2015   Bhatia et al.
2021/0023146 A1*  1/2021   Zhang .................... A61P 37/04

FOREIGN PATENT DOCUMENTS

| CN | 1735431 A | 2/2006 |
|----|-----------|--------|
| CN | 101953855 A | 1/2011 |
| CN | 104906143 A | 9/2015 |
| CN | 105504054 A | 4/2016 |
| WO | 2015056770 A1 | 4/2015 |
| WO | WO-2015056770 A1 * | 4/2015 ........... A61K 35/744 |

OTHER PUBLICATIONS

Detmer et al, Microbial Cell Factories 2006, 5:23 doi:10.1186/1475-2859-5-23, published: Jun. 23, 2006 (Year: 2006).*
Donkor et al, Clinical and Experimental Immunology, 2012, 167:282-295 (Year: 2012).*
Sim et al, J. Microbiol. Biotechnol. (2018),28(6), 883-892. first published online: Apr. 12, 2018 (Year: 2018).*
Vilander et al, Vaccines 2019, 7, 150; doi:10.3390/vaccines7040150. Published: Oct. 16, 2019 (Year: 2019).*
Wang et al, Microbiol Immunol. 2013, 57"54-62 (Year: 2013).*
Guangwei Su et al., The Influence of Peptidoglycan of Lactobacillus on Immune Function of Mouse. China Biotechnology, 2006, pp. 98-102, vol. 26 No. 8.
Chao Gu et al., Study on the immunoloregulate effect of cell wall components of Bifidobacterium. Journal of Tianjin Medical University, 2004, pp. 179-181, vol. 10 No. 2.
Yumei Chen et al., Effect of whole peptidoglycan of Bifidobacterium on food allergic mice's regulatory T cells. Chinese Journal of Microecology, 2012, pp. 865-867, vol. 24 No. 10.
Nana Song et al., Research progress of Lactobacillus exopolysaccharides and peptidoglycan on the function of antitumor. Journal of Inner Mongolia Medical College, 2012, pp. 996-999, vol. 34, No. 6.
Wenming Zhang et al., Mechanism of action of probiotic function of Lactobacilli, Chinese Journal of Animal Nutrition, 2012, pp. 389-396, vol. 24 No. 3.
Zhao Liu et al., Research progress in peptidoglycan of lactic acid bacteria, Microbiology China, Jan. 20, 2016, pp. 188-197, vol. 43 No. 1.

* cited by examiner

*Primary Examiner* — Nita M. Minnifield
(74) *Attorney, Agent, or Firm* — Bayramoglu Law Offices LLC

(57) ABSTRACT

An intravenous injection for enhancing immune function is provided, belonging to the field of biomedicine. The main ingredient of the drug is inactivated lactic acid bacteria, which is prepared by inactivating living lactic acid bacteria.

19 Claims, 1 Drawing Sheet

INTRAVENOUS INJECTION FOR ENHANCING IMMUNE FUNCTION

CROSS REFERENCE TO THE RELATED APPLICATIONS

This application is the national phase entry of International Application No. PCT/CN2016/098444, filed on Sep. 8, 2016, the entire contents of which are incorporated herein by reference.

TECHNICAL FIELD

The present invention belongs to the field of biomedicine, and particularly relates to an intravenous injection for enhancing immune function.

BACKGROUND

The body's immune system consists of immune organs (such as spleen, thymus, lymph nodes, etc.), immune cells (such as mononuclear macrophages, lymphocytes, neutrophils, etc.) and immunologically active substances (such as antibodies, complements, interleukins, etc.). The immune system is an important body defense system, which is directly related to the disease resistance of the body. The body can eliminate viruses, bacteria, fungi, parasites, cancer cells, etc. by the immune system to avoid causing diseases. The immune system eliminates pathogens mainly through non-specific immune function and specific immune function. The non-specific immune function refers to a natural resistance to pathogens without specific targeting, which eliminates the pathogens by means of the barrier effect of skin and mucosa, the filtration effect of lymphoid tissue, the phagocytosis of monocyte-macrophage system and the killing effect of lysozyme. The specific immune function refers to lymphocytes targeting a specific antigen and producing a corresponding antibody or performing a local cellular reaction to kill the specific pathogen. For example, after being stimulated by pathogens, T cells are transformed into sensitized lymphocytes, which can directly attack the pathogens with specific antigenicity, thereby playing a role of cellular immunity; after being stimulated by the pathogens, B lymphocytes can be transformed into plasma cells to secrete antibodies, and then immunoreaction, such as neutralization, precipitation, agglutination or dissolution, is occurred between the antibodies and the pathogens, thereby playing a role of humoral immunity.

If the body's immune function is weak, the body's defense mechanism will be weak, easily causing infection by pathogenic microorganisms or parasites, occurrence of cancer, etc. Many factors can weaken the body's immune function. If the body suffers from stress reaction, long-term fatigue, stressful work or exposure to radiation from radioactive substances, the immune function may be weakened; some drugs can inhibit the body's immune function, such as dexamethasone, cyclophosphamide, cyclosporine, chloramphenicol, sulfonamides, etc.; some toxins can inhibit the immune function as well, such as aflatoxins, ochratoxin, etc. In addition, many diseases can cause immunosuppression of the body inherently, such as acquired immune deficiency syndrome (AIDS), malignant tumors, nodular leprosy, tertiary syphilis, advanced tuberculosis, strongyloidiasis, etc., in human clinics. In veterinary clinics, there are many immunosuppressive diseases as well, such as equine infectious anemia, bovine leukemia, peste des petits ruminants in goats, porcine reproductive and respiratory syndrome, porcine circovirus disease, avian reticuloendotheliosis, Marek's disease in chicken, canine distemper, canine parvovirus disease, etc.

The drugs currently used to improve the body's immune function mainly include: polysaccharides, such as Astragalus polysaccharide, lentinan, Coriolus versicolor polysaccharide, ginseng polysaccharide, Tremella polysaccharide, polyporus polysaccharide, etc.; cytokines, such as interferon-α, interferon-β, interferon-γ, recombinant interleukin-2, thymosin, transfer factor, colony stimulating factor, spleen polypeptide, etc.; antibodies, such as egg-yolk antibodies, serum antibodies, monoclonal antibodies, gamma globulins, etc.; traditional Chinese medicines, such as Yu-Ping-Feng-San (Jade Wind-Barrier Powder), Cordyceps sinensis, propolis, etc.; vitamins, such as vitamin C, folic acid, vitamin $B_{12}$, vitamin A, etc.; trace elements, such as zinc gluconate, sodium selenite, iron dextran, etc.; and chemicals, such as levamisole, isoprinosine, pidotimod, etc.

In addition to the above-mentioned immunomodulatory drugs, more and more drugs use microorganisms and the active components or metabolites thereof as immunomodulators. However, most of the immunomodulators are preparations made of the bacterial components or metabolites of the weakened or inactivated harmful bacteria or non-probiotics. For example, Bacillus Calmette-Guerin (BCG) vaccine, which is a vaccine against tuberculosis, has immunity-enhancing effects and can be used for the adjuvant treatment of preventing tuberculosis and tumors by oral administration, subcutaneous injection, intraperitoneal injection or intratumor injection. *Corynebacterium parvum* preparation is a dead bacteria suspension solution of *Corynebacterium parvum*, which can improve the non-specific immune function of the body, and is used for the adjuvant treatment of some tumors by subcutaneous injection, intramuscular injection, intratumor injection, intravenous infusion, etc. Group A *Streptococcus* preparation, which is a bacterial preparation of freeze-dried low-virulence mutant Su-strain of type III group A hemolytic streptococcus, still containing penicillin G potassium salt, etc., has the functions of directly killing tumor cells and activating host immune function, and is used for the adjuvant treatment of cancer by subcutaneous injection, intramuscular injection, intratumor injection, intravenous injection, etc. *Pseudomonas aeruginosa* preparation, which is made by inactivated piliated strains of *Pseudomonas aeruginosa* bacterium, can regulate the body's immune function, and can be used for adjuvant treatment by subcutaneous injection or tumor local injection. *Mycobacterium phlei* preparation, whose main ingredient is inactivated *Mycobacterium phlei*, is used for the treatment of diseases characterized by decreased immune function, such as chronic bronchitis, tumor, hepatitis, diabetes, pulmonary tuberculosis and extrapulmonary tuberculosis, etc., by deep intramuscular injection. In addition, whole bacterial cells of genus *Rhodococcus*, genus *Gordonia*, genus *Nocardia*, genus *Dietzia*, genus *Tsukamurella*, and genus *Nocardioides* have been used as immunomodulators (Patent Publication No. CN1735431A). The drugs used for immunomodulation, whose ingredients are obtained by processing some harmful bacteria, include: an injection of *Nocardia rubra* cell wall skeleton for adjuvant treatment of cancer, which is prepared by fermentation, crushing and extraction of *Nocardia rubra* to obtain the cell wall skeleton (N-CWS), and then freeze-drying with an appropriate amount of emulsifier, mainly containing the components of the cell wall of *Nocardia rubra*, such as mycolic acid, arabinogalactan, mucopeptides, etc. BCG polysaccharide nucleic acid preparation, which is made of polysaccharides and nucleic acids extracted from BCG, can prevent and treat chronic bronchitis, cold and asthma by intramuscular injection. Mannatide, an α-mannan extracted from the culture medium of Group A Streptococci, is used as an immunopotentiator for the adjuvant treatment during tumor radiotherapy and chemotherapy. Bacterial lysates preparation, containing bacterial lysates extracted from eight species of bacteria hydrolyzed by alkaline protease, i.e., *Haemophilus influenzae, Pneumococci, Klebsiella pneumoniae, Klebsiella ozaenae, Staphylococcus aureus, Streptococcus pyogenes, Streptococcus viridans,* and *Neisseria catarrhal,* is an immunostimulant for preventing recurrent respiratory tract infections and acute exacerbations of chronic bronchitis by oral administration. *Typhoid bacillus* lipopolysaccharide preparation, which is prepared by enzymatic digestion and extraction of *Typhoid bacillus* cultures, is used for chronic bronchitis patients, and has certain curative effect on controlling the occurrence of cold and alleviating illness. *Staphylococcus aureus* filtrate preparation, a yellowish clear liquid obtained from fermentation culture of a *Staphylococcus aureus* strain isolated from pus of a patient with chronic osteomyelitis by removing the bacterial cells, is an extracellular protein product of *Staphylococcus aureus,* whose one active ingredient is enterotoxin C. The *Staphylococcus aureus* filtrate preparation has immunomodulatory effects and can be used for adjuvant treatment of malignant tumors by intramuscular injection or intraperitoneal injection. In addition, some people use inactivated avian *Tuberculosis bacillus* as an immunizing antigen for immunization conducted with an intravenous injection method via rabbit ear-rim auricular vein to prepare high-titer serum (Patent Publication No. CN105504054A).

All of the above immunomodulators are prepared by harmful bacteria or non-probiotics and components or metabolites thereof. However, the research on using beneficial bacteria (i.e., probiotics) as immunomodulators has received increasing attention. Probiotics are a generic term for a class of active microorganisms that have a beneficial effect on the host health. Among the probiotics, the research on lactic acid bacteria has received more attention. Lactic acid bacteria is a general term for a class of nonsporulating and Gram-positive bacteria, who ferment sugar to produce lactic acid as the main product. Lactic acid bacteria play an important role in maintaining the health of human and animals. At present, a large number of studies have confirmed that oral administration of living lactic acid bacteria can improve the body's immune function. Other researchers have found that some inactivated lactic acid bacteria still have biological functions, for example, cells of inactivate lactic acid bacteria still have adhesion property to cells of human colonic adenocarcinoma cell line Caco-2 cultured in vitro and physiological activities such as efficacy of promoting animal growth when used as a feed additive, etc. (Patent Publication No. CN104906143A). In addition, the bacterial components constituting the lactic acid bacteria have certain physiological functions or pharmacological effects as well. For example, administrating the mice with *Enterococcus faecalis* cell wall lysates obtained by processing under high temperature and high pressure by intraperitoneal injection can enhance the phagocytic ability of macrophages (Patent Publication No. CN101953855A). Other researchers have found that genomic DNA (deoxyribonucleic acid) of lactic acid bacteria can suppress allergic reaction in human by shifting the Th1/Th2 balance (Patent Publication No. US2014/0288159A1). Other researchers have reported that the cell wall component peptidoglycan or intact peptidoglycan of lactic acid bacteria has immunomodulatory, anti-allergic or anti-tumor effects by oral administration, subcutaneous injection or intraperitoneal injection (Reference [1]: Guangwei Su, Jin Sun, Yonghui Shi, Guowei L E. The Influence of Peptidoglycan of *Lactobacillus* on Immune Function of Mouse. China Biotechnology, 2006, 26(8):98-102. Reference [2]: Chao gu, Zhirui Wang, Junfei Wei, Lixue Song, Jingying Chen. Study on the immunoloregulate effect of cell wall components of *Bifidobacterium.* Journal of Tianjin Medical University, 2004, 10(2):179-181. Reference [3]: Yumei Chen, Xi Cheng. Effect of whole peptidoglycan of *Bifidobacterium* on food allergic mice's regulatory T cells. Chinese Journal of Microecology, 2012, 24(10):865-867. Reference [4]: Nana Song, Jinghui Song. Research progress of *Lactobacillus* exopolysaccharides and peptidoglycan on the function of antitumor. Journal of Inner Mongolia Medical College, 2012, 34(6): 996-999.). Other researchers have introduced exogenous gene capable of expressing cytotoxic proteins into *Salmonella, Escherichia coli, Lactobacillus, Bifidobacteria,* etc., and then injected the bacteria intravenously for targeted tumor therapy relied on the quorum sensing (Patent Publication No. US2015/0225692A1).

Compared with harmful bacteria, beneficial bacteria are safer when used as immunomodulators. Harmful bacteria or constituents or metabolites thereof generally have toxic components that are harmful to the body, or actually, the prevention and treatment of diseases is achieved by using the toxic components thereof, thus posing a potential safety risk to the body. Especially by intravenous administration, the adverse reactions will be more obvious. However, lactic acid bacteria contain few or no toxic substances, so that intravenous administration of inactivated lactic acid bacteria is much safer for the body. At present, there is no report on the intravenous administration of inactivated lactic acid bacteria to improve immune function. We have made a bold attempt to conduct a study on the efficacy of intravenous administration of inactivated lactic acid bacteria, and found that it has a strong immune enhancement effect on the body, which has a broad application prospect in the future.

SUMMARY

An injection for enhancing immune function, wherein, the main ingredient of the injection is inactivated lactic acid bacteria. After Gram staining of the inactivated lactic acid bacteria in the injection, the inactivated lactic acid bacteria are observed to maintain intact bacterial morphology under an oil immersion lens. Maintaining intact bacterial morphology as described herein means substantially consistent with the living cells before inactivation in outline and morphology. Substantially consistent means that slight changes in cell walls of the cells may occur during the inactivation of the lactic acid bacteria, such as a loss of partial surface components, but the changes are minor or rare.

A number of intact cells of the inactivated lactic acid bacteria per milliliter of the injection is $10^5$ -$10^{12}$.

The lactic acid bacteria are selected from the group consisting of genus *Lactobacillus,* genus *Enterococcus,* genus *Lactococcus,* genus *Bifidobacterium,* genus *Leuconostoc,* and genus *Streptococcus.*

Further, an inactivation method of the lactic acid bacteria is one method selected from the group consisting of high temperature inactivation, high temperature and high-pressure inactivation, ultraviolet inactivation, chemical inactivation, and radiation inactivation.

Furthermore, the injection further includes a pharmaceutically acceptable adjuvant, and the adjuvant contains sufficient salt or monosaccharide to ensure that osmotic pressure of a suspension solution of the injection is the same or similar to that of blood.

In the present invention, dosage forms of the inactivated lactic acid bacteria injection includes: a powder injection, a suspension injection, etc. The powder injection is prepared by spray drying or freeze drying, and is prepared into a suspension solution during administration.

The injection is an intravenous injection.

Preferably, the inactivated lactic acid bacteria are a single species. After Gram staining of the inactivated lactic acid bacteria, the inactivated lactic acid bacteria are observed to maintain intact bacterial morphology under an oil immersion lens, and are consistent with the living cells before inactivation in outline and morphology. An administration method of the medicine is intravenous administration.

Further, the inactivated lactic acid bacteria are a mixture of at least two species of inactivated lactic acid bacteria. After Gram staining of the inactivated lactic acid bacteria, most of the inactivated lactic acid bacteria are observed to maintain intact bacterial morphology under an oil immersion lens. An administration method of the medicine is intravenous administration. The inactivated lactic acid bacteria are obtained by one method selected from the group consisting of high temperature and high-pressure inactivation, ultraviolet inactivation, chemical inactivation, and radiation inactivation. The lactic acid bacteria are selected from the group consisting of genus *Lactobacillus*, genus *Enterococcus*, genus *Lactococcus*, genus *Bifidobacterium*, genus *Leuconostoc*, and genus *Streptococcus*.

DNA is extracted from the inactivated lactic acid bacteria, and a species of the lactic acid bacteria can be identified by gene sequencing or by PCR amplification and sequencing of a target fragment such as 16S rDNA, etc.

Further, the inactivated lactic acid bacteria are selected from the following lactic acid bacteria after an inactivation treatment: (1) genus *Lactobacillus*: *L. delbrueckii*, *L. bulgaricus*, *L. helviticus*, *L. acido phlus*, *L. gasseri*, *L. salivarius*, *L. plantarum*, *L. reuteri*, *L. brevis*, *L. casei*, *L. fermentum*, etc.; (2) genus *Leuconostoc*: *L. mesteneroides*, *L. cremoris*, *Leuc. dextranicun*, *L. lactis*, *L. oenos*, etc.; (3) genus *Enterococcus*: *E. faecium*, *E. faecalis*, etc.; (4) genus *Lactococcus*: *L. lactis* subsp. *lactis*, *L. lactis* subsp. *cremoris*, *L. lactis* subsp. *hordniae*, etc.; (5) genus *Streptococcus*: *S. lactis*, *S. diacetilactis*, *S. creamoris*, *S. thermophilus*, etc.; (6) genus *Bifidobacterium*: *B. bifidum*, *B. longum*, *B. breve*, *B. infantis*, *B. adolescentis*, *B. animalis*, etc.; and (7) Lactic acid bacteria of other genus or species.

The adjuvant for the intravenous injection is selected from the group consisting of octylphenoxy polyethoxyethanol, tyloxapol, polyethylene glycol sorbitan monooleate, polyoxyethylene monostearate, polyoxyethylene derivative, Tween-80, sodium polyalkyl benzene sulfonate, sodium lauryl sulfate, alkali metal polysaccharide sulfates, dextran sulfate sodium, dioctyl sulfosuccinate, acacia gum, Arabic gum, polyvinylpyrrolidone, polyethyl silicate, ethanol, glycerin, sorbitol, honey, agar, starch, dextrose, fructose, malt extract, cocoa powder, tartaric acid, citric acid, sodium citrate, carragenates, alginic acid, sodium alginate, tannin, cyclohexylaminesulfonic acid, mineral oil, eucalin, sodium saccharin, Indian gum, karaya gum, gum tragacanth, pectin, carrageenan, gelatin, carboxymethyl cellulose, cellulose sulfate, methyl cellulose, sodium carboxymethyl cellulose, sodium cellulose acetate sulfate, sodium hydroxyethyl cellulose, polymethylsilane, potassium sorbate, kaolin, diatomaceous earth, bentonite, aluminum silicate, aluminum hydroxide, colloidal aluminum hydroxide, magnesium aluminum silicate, magnesium montmorillonite, magnesium trisilicate, sodium aluminum magnesium silicate, sodium hydrogen carbonate, sodium carbonate, methylparaben, propylparaben, ethyl vanillin, lemon oil, orange-peel oil, vanillin, casein, etc.

Preferably, the lactic acid bacteria of the present invention are selected from the group consisting of: *Lactococcus lactis* subsp. *Lactis* (accession number: CICC 6246), *Lactobacillus plantarum* subsp. *Plantarum* (accession number: CICC 6240), *Bifidobacterium longum* (accession number: CICC 6196), *Lactobacillus brevis* (accession number: CICC 6239), and *Enterococcus faecium* (accession number: CICC 6049). The above five species of lactic acid bacteria were inactivated by conventional methods, and then intravenously administered to mice. It was found that the above five species of inactivated lactic acid bacteria could enhance the immune function of the mice. Thereafter, the isolated *Enterococcus faecium* was selected and studied in detail, and was found that the inactivated *Enterococcus faecium* could still be Gram stained and the inactivated *Enterococcus faecium* was observed to maintain the same outline and morphology as the living *Enterococcus faecium* under the oil immersion lens. Then, the inactivated *Enterococcus faecium* physiological saline suspension solution was centrifuged, the supernatant was discarded, and the DNA was extracted. The 16S rDNA gene fragment could still be amplified by PCR, and the species of the lactic acid bacteria could be identified by sequencing.

Further studies have found that intravenous administration of inactivated *Enterococcus faecium* can effectively improve the non-specific immune function and specific immune function of normal mice and immunocompromised mouse models, and can increase the weight of immune organs in the body as well.

The inactivated lactic acid bacteria intravenous injection provided by the present invention can be used for the prevention, treatment or adjuvant treatment of various diseases such as various bacterial diseases, viral diseases, fungal diseases, parasitic diseases, cancers, and body immune dysfunction caused by various reasons in humans or animals.

No one has attempted to improve the immune function of the body by intravenously administrating inactivated lactic acid bacteria before, mainly considering the safety of intravenous administration of the inactivated lactic acid bacteria. Compared with the water-soluble intravenous injection used daily, the inactivated lactic acid bacteria intravenous injection is a granular suspension solution, and intravenous administration of the granular substance has a higher risk. Some studies have suggested that the intravenous administration of cells and components of harmful bacteria can treat diseases in a "attacking the toxifying disease with poisonous agents" way, while beneficial bacteria are difficult to have such effect. After a long-term study, the present invention has found that intravenous administration of the inactivated lactic acid bacteria has a strong immune-enhancing effect on the body, and can exert the effect of "enhancing immunity and detoxification".

Some previous studies have reported that surface components of lactic acid bacteria, such as lipoteichoic acid (LTA), cell wall peptidoglycan (PG), cell surface protein (S-protein), and some unknown surface extracts, can be used as ligands to activate the immune signaling pathway after being recognized by Toll-like receptors, thus enhancing the body's immune function (Reference [5]: Wenming Zhang, Haifeng Wang, Jianxin Liu. Mechanism of action of probiotic function of Lactobacilli, Chinese Journal of Animal Nutrition, 2012, 24(3):389-396). In particular, peptidoglycan, the surface substance of lactic acid bacteria, is an essential component of the cell wall of the lactic acid bacteria, which is an important substance that enables the lactic acid bacteria to activate the immune system by acting on the Toll-like receptors as well (Reference [6]: Zhao Liu, Jianjun Qiao, Hongji Zhu. Research progress in peptidoglycan of lactic acid bacteria. Microbiology China, 2016, 43(1):188-197). In the present invention, the lactic acid bacteria are not used to extract the above-mentioned surface components, but are directly inactivated according to a conventional method, and then an intravenous administration is performed, which can improve the body's immune function. Moreover, it has been found that the inactivated lactic acid bacteria maintain the same cell outline and morphology as the living lactic acid bacteria before inactivation, and further confirmed that intravenous injection of inactivated representative strains of different genera of the lactic acid bacteria (such as *Lactococcus lactis* subsp. *lactis, Lactobacillus plantarum* subsp. *Plantarum, Bifidobacterium longum, Lactobacillus brevis,* and *Enterococcus faecium*), can improve the body's immune function, indicating that the intravenous administration of inactivated lactic acid bacteria can activate the immune system universally.

Therefore, we speculate that although the lactic acid bacteria are inactivated, the surface components of the intact cell outline can still be recognized by the Toll-like receptors on the immune cells, thereby activating the immune system. Thus, the advantages of intravenous administration of the inactivated lactic acid bacteria as an immunopotentiator are that: it is not necessary to extract the surface components of the lactic acid bacteria to regulate the immune function, but directly inactivate the lactic acid bacteria, so the method is simple; moreover, the inactivated lactic acid bacteria can flow into the immune organs such as thymus, spleen, lymph nodes, etc. as the blood flows, and directly act on Toll-like receptors on immune cells, and therefore the immune activation of the inactivated lactic acid bacteria is more powerful and rapid.

DETAILED DESCRIPTION OF THE EMBODIMENTS

Embodiment 1

Figure 1:
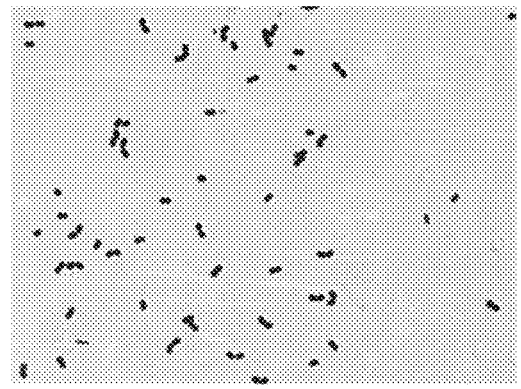
FIG. 1 is an observation view of living *Enterococcus faecium* after being Gram-stained, under an oil immersion lens.
Figure 2:
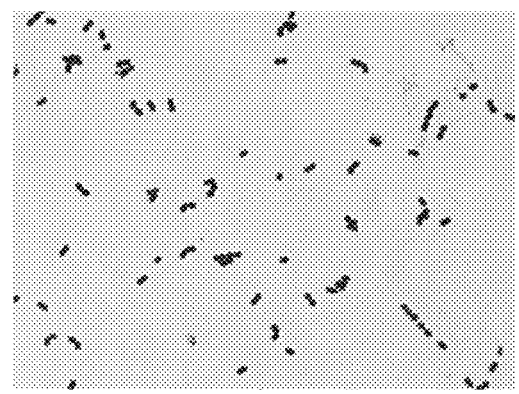
FIG. 2 is an observation view of inactivated *Enterococcus faecium* after being Gram-stained, under an oil immersion lens.
Figure 3:
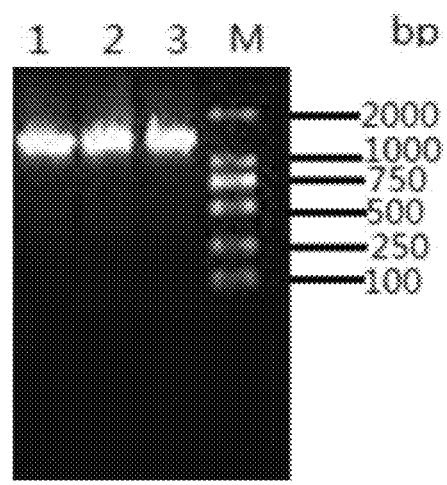
FIG. 3 is an electropherogram of PCR-amplified 16S rDNA of *Enterococcus faecium;* wherein, M is Marker; 1, 2 and 3 are bands of three repetitive PCR-amplified 16S rDNA of inactivated *Enterococcus faecium.*

*Enterococcus faecium* (purchased from China Center of Industrial Culture Collection, CICC ; accession number: CICC 6049) was inoculated into deMan Rogosa Sharpe (MRS) medium, cultured in a 37° C. incubator for 24 hours, and then centrifuged at 3000 rpm for 5 minutes. The supernatant medium was discarded and the precipitate was retained. The precipitate was washed with sterile physiological saline and centrifuged for 5 minutes. After repeated washing for 3 times, the sterile physiological saline was added and mixed evenly with the precipitate to prepare a suspension solution. A certain amount of the *Enterococcus faecium* physiological saline suspension solution was taken and the OD value thereof was measured at 690 nm by the spectrophotometer. When the final concentration of the suspension solution diluted with the sterile physiological saline has an OD value of 0.38, such a diluted concentration of the *Enterococcus faecium* physiological saline suspension solution was taken as one time (1×) concentration. The bacteria were counted on a Thoma bacterial counting chamber to obtain a total of about $10^8$ *Enterococcus faecium* intact cells per milliliter of the suspension solution at this concentration. A small amount of 1× concentration of the *Enterococcus faecium* physiological saline suspension solution was taken for Gram staining, and the morphology of the living bacteria was observed under an oil immersion lens (see FIG. 1). The prepared 1× concentration of *Enterococcus faecium* physiological saline suspension solution was inactivated at 121° C. and a pressure of 0.12 MPa for 15 minutes to obtain an inactivated *Enterococcus faecium* injection. A small amount of inactivated *Enterococcus faecium* injection was taken for Gram staining, and the morphology of the inactivated cells was observed under an oil immersion lens (see FIG. 2). In comparison, it was found that the inactivated bacteria were consistent with the living bacteria in outline and morphology, and the bacterial count showed that the number of the cells did not change significantly before and after the inactivation. The inactivated *Enterococcus faecium* physiological saline suspension solution was centrifuged, the supernatant was discarded, the precipitate was retained, the DNA was extracted, 16S rDNA was amplified by PCR, and the agarose gel electrophoresis was performed (see FIG. 3). Identification of the species of the lactic acid bacteria can further be performed by sequencing.

Embodiment 2

*Enterococcus faecium* (purchased from China Center of Industrial Culture Collection, CICC; accession number: CICC 6049) was inoculated into deMan Rogosa Sharpe (MRS) medium, cultured in a 37° C. incubator for 24 hours, and then centrifuged at 3000 rpm for 5 minutes. The supernatant medium was discarded and the precipitate was retained. The precipitate was washed with 0.9% sterile physiological saline and centrifuged for 5 minutes. After repeated washing for 3 times, an appropriate amount of 0.9% sterile physiological saline was added and mixed evenly with the precipitate to prepare a suspension solution. A certain amount of the lactic acid bacteria suspension solution was taken and the OD value thereof was measured at 690 nm by the spectrophotometer. When the final concentration of the suspension solution diluted with the sterile physiological saline has an OD value of 0.38, such a diluted concentration of the lactic acid bacteria suspension solution was taken as one time (1×) concentration. Based on this, the physiological saline solution containing the lactic acid bacteria was diluted in different multiples with the physiological saline solution to obtain 5×, 1×, and 0.2× concentrations of lactic acid bacteria suspention solution. Thereafter, the prepared *Enterococcus faecium* suspension solution with 5×, 1× and 0.2× concentrations were inactivated at 121° C. and a pressure of 0.12 MPa for 15 minutes to obtain the inactivated *Enterococcus faecium* suspension medicaments with 5×, 1× and 0.2× concentrations. The effect of the inactivated Enterococcus faecium intravenous injection on the phagocytosis of mononuclear-macrophages in normal mice was determined by a carbon clearance assay. Clean-grade Kunming mice, weighing 18-22 g, were divided into a normal control group, a thymopentin group (positive drug control group), and high, medium and low doses of inactivated *Enterococcus faecium* groups. Each group had 10 mice, half male and half female. The normal control group was injected with sterile physiological saline via the tail vein; the thymopentin group was injected with 0.2 mg/kg of thymopentin via the tail vein; and the high, medium and low doses of the inactivated *Enterococcus faecium* groups were injected with the inactivated *Enterococcus faecium* suspension solutions with 5×, 1× and 0.2× concentrations via the tail vein. The above-mentioned groups were all administered at a volume of 0.1 mL per 10 g, and were injected via the tail vein for five consecutive days, once a day. Two hours after the administration on the fifth day, the mice were injected with 0.05 mL/10 g of Indian ink via the tail vein. 40 μL blood samples were collected from the orbital venous plexus at 1 min and 10 min, respectively, and were added to 4 mL of 0.1% $Na_2CO_3$ solution and shaken evenly, respectively. The optical density was measured by spectrophotometer at 680 nm wavelength (hereinafter, the optical densities of the blood samples taken at 1 min and 10 min are represented by $OD_1$ and $OD_{10}$, respectively). The carbon clearance index K values were calculated by the following formula. The carbon clearance index $K=(lgOD_1-lgOD_{10})/(t_{10}-t_1)$. The significance of experimental data were tested by SPSS 11.5 software, and the results were shown in Table 1. Table 1 showed that, compared with the normal control group, the carbon clearance index K values of the high, medium and low doses of inactivated *Enterococcus faecium* groups were extremely significantly increased; moreover, compared with the positive drug thymopentin group, the carbon clearance index K values of the high, medium and low doses of inactivated *Enterococcus faecium* groups were still extremely significantly increased. The above results showed that intravenous administration of inactivated *Enterococcus faecium* can improve the phagocytosis of monocytes-macrophages in normal mice, namely, improve the non-specific immune function of the mice.

TABLE 1

Effect of intravenous administration of inactivated *Enterococcus faecium* on phagocytosis of monocytes-macrophages in normal mice

| Group | Dose | Carbon clearance index K × 10³ |
|---|---|---|
| Normal control group | 0 | 4.773 ± 1.249 |
| Thymopentin group | 0.2 mg/kg | 4.874 ± 0.582 |
| High dose of inactivated *Enterococcus faecium* group | 5× | 7.702 ± 1.128**ΔΔ |
| Medium dose of inactivated *Enterococcus faecium* group | 1× | 7.905 ± 1.3148**ΔΔ |
| Low dose of inactivated *Enterococcus faecium* group | 0.2× | 7.004 ± 1.400**ΔΔ |

Note:
**indicates an extremely significant difference P < 0.01 compared with the normal control group, and
* indicates a significant difference P < 0.05 compared with the normal control group;
ΔΔindicates an extremely significant difference P < 0.01 compared with the thymopentin group, and
Δ indicates a significant difference P < 0.05 compared with the thymopentin group.

Embodiment 3

The inactivated *Enterococcus faecium* suspension solutions with 5×, 1× and 0.2× concentrations in Embodiment 2 were used, the effect of intravenous injection of inactivated *Enterococcus faecium* suspension solutions on the phagocytosis of mononuclear-macrophage in immunosuppressed mouse model was determined by the carbon clearance assay. Clean-grade Kunming mice, weighing 18-22 g, were divided into a normal control group, an immunosuppressed model group, a thymopentin group (positive drug control group), and high, medium and low doses of inactivated *Enterococcus faecium* groups. Each group had 10 mice, half male and half female. The immunosuppressed mouse models were prepared by intraperitoneal injection of dexamethasone at a dose of 40 mg/kg for five consecutive days, once a day. On the day when the immunosuppressive mouse models were prepared, the mice of the normal control group and the immunosuppressive model mice of the immunosuppressed model group were injected with sterile physiological saline via the tail vein, the immunosuppressive model mice of the thymopentin group was injected with 0.2 mg/kg thymopentin via the tail vein, the immunosuppressive model mice of the high, medium and low doses of the inactivated *Enterococcus faecium* groups were injected with the inactivated *Enterococcus faecium* suspension solutions with 5×, 1× and 0.2× concentrations via the tail vein. The above-mentioned groups were all administered at a volume of 0.1 mL per 10 g. The mice of each group were administered for five consecutive days, once a day. Two hours after the last administration the mice were injected with 0.05 mL/10 g of Indian ink via the tail vein. 40 μL blood samples were collected from the orbital venous plexus at 1 min and 10 min, respectively, and were added to 4 mL of 0.1% $Na_2CO_3$ solution and shaken evenly, respectively. The optical density was measured by spectrophotometer at 680 nm wavelength (hereinafter, the optical densities of the blood samples taken at 1 min and 10 min are represented by $OD_1$ and $OD_{10}$ respectively). The carbon clearance index K values were calculated by the following formula. The carbon clearance index $K=(lgOD_1-lgOD_{10})/(t_{10}-t_1)$. The significance of experimental data were tested by SPSS 11.5 software, and the results were shown in Table 2. Table 2 showed that, compared with the normal control group, the carbon clearance index K value of the immunosuppressed model group was significantly reduced, indicating that the immunosuppressed mouse models were successfully prepared; compared with the immunosuppressed model group, the carbon clearance index K values of the high, medium and low doses of inactivated *Enterococcus faecium* groups were extremely significantly or significantly increased; and compared with the thymopentin group, the carbon clearance index K value of the high dose of inactivated *Enterococcus faecium* group was still significantly increased. The above results showed that the intravenous administration of the inactivated *Enterococcus faecium* can improve the phagocytosis of monocytes-macrophages in immunosuppressed mouse models, namely, improve the non-specific immune function of the immunosuppressed mouse models.

TABLE 2

Effect of intravenous administration of inactivated *Enterococcus faecium* on phagocytosis of monocytes-macrophages in immunosuppressed mouse models

| Group | Dose | Carbon clearance index K × 10³ |
|---|---|---|
| Normal control group | 0 | 8.401 ± 2.039 |
| Immunosuppressed model group | 0 | 5.034 ± 1.569** |
| Thymopentin group | 0.2 mg/kg | 7.773 ± 1.018ΔΔ |
| High dose of inactivated *Enterococcus faecium* group | 5× | 9.477 ± 1.852ΔΔ# |

TABLE 2-continued

Effect of intravenous administration of inactivated
Enterococcus faecium on phagocytosis of monocytes-
macrophages in immunosuppressed mouse models

| Group | Dose | Carbon clearance index K × 10³ |
|---|---|---|
| Medium dose of inactivated Enterococcus faecium group | 1× | 7.211 ± 2.613^ΔΔ |
| Low dose of inactivated Enterococcus faecium group | 0.2× | 6.939 ± 1.245^Δ |

Note:
**indicates an extremely significant difference $P < 0.01$ compared with the normal control group, and
* indicates a significant difference $P < 0.05$ compared with the normal control group;
ΔΔindicates an extremely significant difference $P < 0.01$ compared with the immunosuppressed model group, and
Δindicates a significant difference $P < 0.05$ compared with the immunosuppressed model group; and
indicates a significant difference $P < 0.05$ compared with the thymopentin group.

Embodiment 4

The inactivated Enterococcus faecium suspension solution with 1× concentration in Embodiment 2 was used, and the effect of intravenous injection of the inactivated Enterococcus faecium suspension solutions on the specific immune function of normal mice was measured. Clean-grade Kunming mice, weighing 18-22 g, were divided into a control group (i.e., the normal mouse Newcastle virus challenge group) and an inactivated Enterococcus faecium administration group. Each group had 10 mice, half male and half female. The control group was injected with sterile physiological saline via the tail vein; and the inactivated Enterococcus faecium administration group was injected with the inactivated Enterococcus faecium suspension solution with 1× concentration via the tail vein. The mice of each group were all administered at a volume of 0.1 mL per 10 g. At 24 hours after administration for one time, Newcastle disease virus was injected into the mice of each group via the tail vein. After 3 days, blood samples were collected from the orbital venous plexus of the mice, and the antibody level to the Newcastle disease virus was detected by hemagglutination and hemagglutination inhibition assay. The significance of the experimental data were tested by SPSS 11.5 software, and the results were shown in Table 3. Table 3 showed that, compared with the control group, the antibody level to the Newcastle disease virus of the inactivated Enterococcus faecium administration group was significantly increased, indicating that intravenous administration of the inactivated Enterococcus faecium can increase the antibody level to the Newcastle disease virus in normal mice, that is, increase the specific immune function of the normal mice.

TABLE 3

Effect of intravenous administration of inactivated
Enterococcus faecium on antibody level to
the Newcastle disease virus in normal mice

| Group | Dose | Antibody level |
|---|---|---|
| Control group | 0 | 4.6 ± 0.7 |
| Inactivated Enterococcus faecium administration group | 1× | 5.4 ± 0.7* |

Note:
** indicates an extremely significant difference $P < 0.01$ compared with the control group, and
*indicates a significant difference $P < 0.05$ compared with the control group.

Embodiment 5

The inactivated Enterococcus faecium suspension solution with 1× concentration in Embodiment 2 was used, and the effect of intravenous injection of the inactivated Enterococcus faecium suspension solutions on the specific immune function of immunosuppressed mouse model was measured. Clean-grade Kunming mice, weighing 18-22 g, were divided into a control group (i.e., the normal mouse Newcastle disease challenge group), an immunosuppressed model group and an inactivated Enterococcus faecium administration group. Each group had 16 mice, half male and half female. The immunosuppressed mouse model was prepared by intraperitoneal injection of dexamethasone at a dose of 80 mg/kg in mice for 3 consecutive days, once a day. On the day when the immunosuppressive mouse models were prepared, the immunosuppressive model mice of the inactivated Enterococcus faecium administration group were injected with the inactivated Enterococcus faecium suspension solution with 1× concentration via the tail vein; and the mice of the control group and the immunosuppressive model mice of the immunosuppressed model group were injected with sterile physiological saline via the tail vein, with a administration volume of 0.1 mL per 10 g. At 24 hours after the administration, equal amounts of Newcastle disease virus were injected into the the mice via the tail vein. After 3 days, blood samples were collected from the orbital venous plexus of the mice, and the antibody level to the Newcastle disease virus was detected by hemagglutination and hemagglutination inhibition assay. The significance of the experimental data were tested by SPSS 11.5 software, and the results were shown in Table 4. Table 4 showed that, compared with the control group, the antibody titer to the Newcastle disease virus of the immunosuppressed model group was significantly reduced; compared with the immunosuppressed model group, the antibody level to the Newcastle disease virus of the inactivated Enterococcus faecium administration group was significantly increased, while no significant difference between the inactivated Enterococcus faecium administration group and the control group was found. The above results showed that the Newcastle disease antibody in mice of the inactivated Enterococcus faecium administration group returned to normal levels, that is, the intravenous administration of the inactivated Enterococcus faecium can increase the specific immune function of the body of the immunosuppressed mouse.

TABLE 4

Effect of intravenous administration of inactivated
Enterococcus faecium on antibody level to the Newcastle
disease virus in immunosuppressed mouse models

| Group | Dose | Antibody level |
|---|---|---|
| Control group | 0 | 4.06 ± 0.68 |
| Immunosuppressed model group | 0 | 3.31 ± 1.01* |
| Inactivated Enterococcus faecium administration group | 1× | 4.06 ± 0.68^Δ |

Note:
** indicates an extremely significant difference $P < 0.01$ compared with the control group, and
*indicates a significant difference $P < 0.05$ compared with the control group;
ΔΔ indicates an extremely significant difference $P < 0.01$ compared with the immunosuppressed model group, and
Δindicates a significant difference $P < 0.05$ compared with the immunosuppressed model group.

Embodiment 6

The inactivated Enterococcus faecium suspension solutions with 5×, 1× and 0.2× concentrations in Embodiment 2 were used, the effect of intravenous injection of inactivated *Enterococcus faecium* suspension solutions on immune organ index in normal mice was measured. Clean-grade Kunming mice, weighing 18-22 g, were divided into a normal control group, a thymopentin group (positive drug control group), and high, medium and low dose inactivated *Enterococcus faecium* groups. Each group had 10 mice, half male and half female. The normal control group was injected with sterile physiological saline via the tail vein, the thymopentin group was injected with 0.2 mg/kg thymopentin via the tail vein, the high, medium and low dose inactivated *Enterococcus faecium* groups were injected with the inactivated *Enterococcus faecium* suspension solutions with 5×, 1× and 0.2× concentrations via the tail vein. The above-mentioned groups were all administered at a volume of 0.1 mL per 10 g, and were injected via the tail vein for five consecutive days, once a day. Spleen index of the mice was measured 2 hours after the last administration. Spleen index=spleen weight/mouse body weight. The significance of the experimental data were tested by SPSS 11.5 software, and the results were shown in Table 5. Table 5 showed that, compared with the normal control group, the spleen index of the high dose inactivated *Enterococcus faecium* group was extremely significantly increased; moreover, the spleen indexes of the medium and low dose inactivated *Enterococcus faecium* groups had no significant difference compared with the normal control group; compared with the thymopentin group, the spleen index of the high dose inactivated *Enterococcus faecium* group was extremely significantly increased as well. The above results showed that intravenous administration of inactivated *Enterococcus faecium* can promote the increase of the immune organ index in normal mice. The spleen index is an important index to measure the effect of drugs on immune function. The increase of the spleen index indicates that the weight of spleen relative to the body is increased, which is the result of the action of the drugs on immune organs and the expression of enhanced immune function.

TABLE 5

Effect of intravenous administration of inactivated *Enterococcus faecium* on spleen index in normal mice

| Group | Dose | Spleen index (%) |
|---|---|---|
| Normal control group | 0 | 0.563 ± 0.070 |
| Thymopentin group | 0.2 mg/kg | 0.642 ± 0.091 |
| High dose inactivated *Enterococcus faecium* group | 5× | 0.849 ± 0.142**ΔΔ |
| Medium dose inactivated *Enterococcus faecium* group | 1× | 0.609 ± 0.122 |
| Low dose inactivated *Enterococcus faecium* group | 0.2× | 0.464 ± 0.047ΔΔ |

Note:
**indicates an extremely significant difference $P < 0.01$ compared with the normal control group, and
* indicates a significant difference $P < 0.05$ compared with the normal control group;
ΔΔindicates an extremely significant difference $P < 0.01$ compared with the thymopentin group, and
Δ indicates a significant difference $P < 0.05$ compared with the thymopentin group.

Embodiment 7

The inactivated *Enterococcus faecium* suspension solutions with 5×, 1× and 0.2× concentrations in Embodiment 2 were used, the effect of intravenous injection of inactivated *Enterococcus faecium* suspension solutions on immune organ index in immunosuppressed mouse model was measured. Clean-grade Kunming mice, weighing 18-22 g, were divided into a normal control group, an immunosuppressed model group, a thymopentin group (positive drug control group), and high, medium and low dose inactivated *Enterococcus faecium* groups. Each group had 10 mice, half male and half female. The immunosuppressed mouse models were prepared by intraperitoneal injection of dexamethasone at a dose of 40 mg/kg in mice for five consecutive days, once a day. On the day when the immunosuppressive mouse models were prepared, the mice of the normal control group and the immunosuppressive model mice of the immunosuppressed model group were injected with sterile physiological saline via the tail vein, the immunosuppressive model mice of the thymopentin group was injected with 0.2 mg/kg thymopentin via the tail vein, the immunosuppressive model mice of the high, medium and low dose inactivated Enterococcus faecium administration groups were injected with the inactivated Enterococcus faecium suspension solutions with 5×, 1× and 0.2× concentrations via the tail vein. Thereafter, each group was administered intravenously for five consecutive days, once a day. The spleen index of the mice was measured after the last administration. Spleen index=spleen weight/mouse body weight. The significance of the experimental data were tested by SPSS 11.5 software, and the results were shown in Table 6. Table 6 showed that, compared with the normal control group, the spleen index of the model group was significantly reduced; compared with the model group, the spleen index of the high dose inactivated *Enterococcus faecium* administration group was significantly increased; moreover, the spleen indexes of the high dose inactivated *Enterococcus faecium* groups had no significant difference compared with the normal control group, indicating that high dose inactivated *Enterococcus faecium* group can increase the spleen index of the mice in the immunosuppressed model group and return to the normal level.

TABLE 6

Effect of intravenous administration of inactivated *Enterococcus faecium* on spleen index in immunosuppressed mouse models

| Group | Dose | Spleen index (%) |
|---|---|---|
| Normal control group | 0 | 0.563 ± 0.070 |
| Immunosuppressed model group | 0 | 0.379 ± 0.095** |
| Thymopentin group | 0.2 mg/kg | 0.546 ± 0.097ΔΔ |
| High dose inactivated *Enterococcus faecium* group | 5× | 0.633 ± 0.194ΔΔ |
| Medium dose inactivated *Enterococcus faecium* group | 1× | 0.454 ± 0.102* |
| Low dose inactivated *Enterococcus faecium* group | 0.2× | 0.323 ± 0.030**## |

Note:
**indicates an extremely significant difference $P < 0.01$ compared with the normal control group, and
*indicates a significant difference $P < 0.05$ compared with the normal control group;
ΔΔindicates an extremely significant difference $P < 0.01$ compared with the immunosuppressed model group, and
Δ indicates a significant difference $P < 0.05$ compared with the immunosuppressed model group; and
indicates an extremely significant difference $P < 0.01$ compared with the thymopentin group.

Embodiment 8

In the present invention, five species of lactic acid bacteria were purchased from China Center of Industrial Culture Collection (CICC), i.e., *Lactococcus lactis* subsp. *Lactis* (accession number: CICC 6246), *Lactobacillus plantarum* subsp. *plantarum* (accession number: CICC 6240), *Bifidobacterium longum* (accession number: CICC 6196), *Lactobacillus brevis* (accession number: CICC 6239), and *Entero-* coccus faecium (accession number: CICC 6049), respectively. 5× concentration of inactivated lactic acid bacteria intravenous injection of the above five species of lactic acid bacteria were prepared according to the method of Embodiment 1, the effect of intravenous injection of the five species of inactivated lactic acid bacteria and the mixture thereof on the phagocytosis of mononuclear-macrophage in mice was measured by the carbon clearance assay. Clean-grade Kunming mice, weighing 18-22 g, were divided into a normal control group, an inactivated *Lactococcus lactis* subsp. *Lactis* group (positive drug control group), an inactivated *Lactobacillus plantarum* subsp. *plantarum* group, an inactivated *Bifidobacterium longum* group, an inactivated *Enterococcus faecium* group, an inactivated *Lactobacillus brevis* group and a mixture group of two inactivated lactic acid bacteria (i.e., a mixture group of the inactivated *Enterococcus faecium* and the inactivated *Lactobacillus brevis* in equal proportion). Each group had 10 mice, half male and half female. The normal control group was injected with sterile physiological saline via the tail vein, the five different inactivated lactic acid bacteria groups and the mixture group of two inactivated lactic acid bacteria were injected with the corresponding drugs via the tail vein. The above-mentioned groups were all administered at a volume of 0.1 mL per 10 g, and were injected via the tail vein for five consecutive days, once a day. Two hours after the administration on the fifth day, the mice were injected with 0.05 mL/10 g of Indian ink via the tail vein. 40 μL blood samples were collected from the orbital venous plexus at 1 min and 10 min, respectively, and were added to 4 mL of 0.1% $Na_2CO_3$ solution and shaken evenly respectively. The optical densities were measured by spectrophotometer at 680 nm wavelength (hereinafter, the optical densities of the blood samples taken at 1 min and 10 min is represented by $OD_1$ and $OD_{10}$ respectively). The carbon clearance index K value was calculated by the following formula. The carbon clearance index $K=(lgOD_1-lgOD_{10})/(t_{10}-t_1)$. The significance of the experimental data were tested by SPSS 11.5 software, and the results were shown in Table 7. Table 7 showed that, compared with the normal control group, the five different inactivated lactic acid bacteria groups and the mixture group of two inactivated lactic acid bacteria all significantly or extremely significantly enhanced the phagocytosis of the monocyte-macrophages in the mice, indicating that intravenous administrations of different species of inactivated lactic acid bacteria and the mixture thereof can all enhance the non-specific immune function of the mice.

TABLE 7

Effect of intravenous administration of five species of inactivated lactic acid bacteria and the mixture thereof on phagocytosis of monocytes-macrophages in mice

| Group | Dose | Carbon clearance index K × $10^3$ |
|---|---|---|
| Normal control group | 0 | 7.261 ± 1.642 |
| Inactivated *Lactococcus lactis* subsp. *Lactis* group | 5× | 9.085 ± 0.877* |
| Inactivated *Lactobacillus plantarum* subsp. *plantarum* group | 5× | 11.548 ± 1.097** |
| Inactivated *Bifidobacterium longum* group | 5× | 9.188 ± 2.551* |
| Inactivated *Enterococcus faecium* group | 5× | 10.328 ± 1.847** |
| Inactivated *Lactobacillus brevis* group | 5× | 9.263 ± 0.656* |

TABLE 7-continued

Effect of intravenous administration of five species of inactivated lactic acid bacteria and the mixture thereof on phagocytosis of monocytes-macrophages in mice

| Group | Dose | Carbon clearance index K × $10^3$ |
|---|---|---|
| Mixture group of two inactivated lactic acid bacteria | 5× | 11.335 ± 1.436** |

Note:
**indicates an extremely significant difference $P < 0.01$ compared with the normal control group, and
*indicates a significant difference $P < 0.05$ compared with the normal control group.

Embodiment 9

According to immunological theory, enhanced immune function is beneficial to the body to clear pathogens to avoid infection. The inactivated *Enterococcus faecium* intravenous injection with 1× concentration in Embodiment 2 was used, and the preventive and therapeutic effect of inactivated *Enterococcus faecium* intravenous injection on mice infected with *Salmonella* was measured. Clean-grade Kunming mice, weighing 18-22 g, were divided into three groups, i.e., a normal control group, a *Salmonella* group and an inactivated *Enterococcus faecium* group. Each group had 30 mice, half male and half female. The mice of the normal control group and the *Salmonella* group were injected with sterile physiological saline via the tail vein; and the inactivated *Enterococcus faecium* group was injected with the inactivated *Enterococcus faecium* suspension solution with 1× concentrations via the tail vein. The mice of each group were all administered at a volume of 0.1 mL per 10 g. At 24 hours after administration, the mice of the *Salmonella* group and the inactivated *Enterococcus faecium* group were injected with *Salmonella enteritidis* (China Veterinary Culture Collection Center, accession number: CVCC 3377). The mice were observed for 7 consecutive days, and the death number of the mice was recorded. The chi-square test was performed on the experimental data using SPSS 11.5 software, and the results were shown in Table 8. Table 8 showed that, compared with the *Salmonella* group, the death number of the mice in the inactivated *Enterococcus faecium* group was significantly reduced, which indicating that the intravenous administration of inactivated *Enterococcus faecium* has a preventive and therapeutic effect on the mice infected with *Salmonella*.

TABLE 8

Result of intravenous administration of inactivated *Enterococcus faecium* to control the lethal effect of *Salmonella* on mice

| Group | Dose | Death number of mice | | | | | | | Total number of deaths |
| | | $1^{st}$ day | $2^{nd}$ day | $3^{rd}$ day | $4^{th}$ day | $5^{th}$ day | $6^{th}$ day | $7^{th}$ day | |
|---|---|---|---|---|---|---|---|---|---|
| Normal control group | 0 | 0 | 0 | 0 | 0 | 0 | 0 | 0 | 0 |
| *Salmonella* group | 0 | 0 | 0 | 5 | 6 | 4 | 4 | 5 | 24** |

TABLE 8-continued

Result of intravenous administration of inactivated *Enterococcus faecium* to control the lethal effect of *Salmonella* on mice

| Group | Dose | \multicolumn{7}{c}{Death number of mice} | Total number of deaths |
|---|---|---|---|---|---|---|---|---|---|

| Group | Dose | 1st day | 2nd day | 3rd day | 4th day | 5th day | 6th day | 7th day | Total number of deaths |
|---|---|---|---|---|---|---|---|---|---|
| Inactivated *Enterococcus faecium* group | 1× | 0 | 1 | 1 | 2 | 5 | 2 | 1 | 12**ΔΔ |

Note:
**indicates an extremely significant difference $P < 0.01$ compared with the normal control group, and
* indicates a significant difference $P < 0.05$ compared with the normal control group;
ΔΔindicates an extremely significant difference $P < 0.01$ compared with the *Salmonella* group and
Δindicates a significant difference $P < 0.05$ compared with the *Salmonella* group.

Embodiment 10

The inactivated *Enterococcus faecium* suspension solutions with 5×, 1× and 0.2× concentrations in Embodiment 2 were used, the effect of inactivated *Enterococcus faecium* intravenous injection on the death number of the mice infected with influenza virus PR8 strain was measured. Clean-grade Kunming mice, weighing 18-22 g, were divided into a normal control group, a PR8 strain model group (i.e., influenza virus PR8 strain infected mouse model group), and high, medium and low dose inactivated *Enterococcus faecium* administration groups. Each group had 30 mice, half male and half female. The high, medium and low dose inactivated *Enterococcus faecium* groups were injected with the inactivated *Enterococcus faecium* suspension solutions with 5×, 1× and 0.2× concentrations via the tail vein, respectively; and the normal control group and the PR8 strain model group were injected with sterile physiological saline via the tail vein. The above-mentioned groups were all administered at a volume of 0.1 mL per 10 g. At 24 hours after administration for one time, except the normal control group, each mouse of the other groups were intranasally inoculated with 0.05 mL of chicken embryo allantoic fluid containing influenza virus PR8 strain under mild anesthesia with ether, so that the influenza virus PR8 strain was infected the mice. Thereafter, the death number of the mice in each group within 10 days was observed and recorded. The chi-square test was performed on the experimental data using SPSS 11.5 software, and the results were shown in Table 9. Table 9 showed that, compared with the PR8 strain model group, the death numbers of the mice in the high and medium inactivated *Enterococcus faecium* administration groups were extremely significantly reduced, and the death numbers of the mice in the low dose inactivated *Enterococcus faecium* administration group was significantly reduced. The above results showed that intravenous administration of the inactivated *Enterococcus faecium* can be used for the prevention and treatment of viral diseases.

TABLE 9

Effect of intravenous administration of inactivated *Enterococcus faecium* on mice infected with influenza virus PR8 strain

| Group | Dose | Cases of mice | Death number |
|---|---|---|---|
| Normal control group | 0 | 30 | 0 |
| PR8 strain model group | 0 | 30 | 25** |
| High dose inactivated *Enterococcus faecium* group | 5× | 30 | 5*ΔΔ |
| Medium dose inactivated *Enterococcus faecium* group | 1× | 30 | 9**ΔΔ |
| Low dose inactivated *Enterococcus faecium* group | 0.2× | 30 | 16**Δ |

Note:
**indicates an extremely significant difference $P < 0.01$ compared with the normal control group, and
*indicates a significant difference $P < 0.05$ compared with the normal control group;
ΔΔindicates an extremely significant difference $P < 0.01$ compared with the PR8 strain model group, and
Δindicates a significant difference $P < 0.05$ compared with the PR8 strain model group.

Embodiment 11

The inactivated *Enterococcus faecium* suspension solutions with 5×, 1× and 0.2× concentrations in Embodiment 2 were used, the effect of intravenous injection of inactivated *Enterococcus faecium* suspension solutions on body weight and spleen index in mice with ascites carcinoma was measured. ICR (Institute of Cancer Research) mice, weighing 18-22 g, were divided into five groups, i.e., an ascites carcinoma model group, a thymopentin group, and high, medium and low dose inactivated *Enterococcus faecium* administration groups. Each group had 10 ascites carcinoma model mice. The mice of the ascites carcinoma model group were injected with sterile physiological saline via the tail vein; the mice of the thymopentin group were injected with 0.2 mg/kg of thymopentin via the tail vein; and the mice of the high, medium and low dose inactivated *Enterococcus faecium* administration groups were injected with the inactivated *Enterococcus faecium* suspension solutions with 5×, 1× and 0.2× concentrations via the tail vein, respectively. The above-mentioned groups were all administered at a volume of 0.1 mL per 10 g. Administration for one time was performed one day before the preparation of the Ehrlich ascites carcinoma (EAC) mouse model, namely, at 24 hours after the administration, the mice were intraperitoneally inoculated with the cell suspension of the Ehrlich ascites carcinoma to prepare the EAC mouse models. Thereafter, administration was performed for 7 consecutive days, and the body weight gain and spleen index of the ascites carcinoma mice were measured. Spleen index=spleen weight/mouse body weight. The significance of the experimental data were tested by SPSS 11.5 software, and the results were shown in Table 10. Table 10 showed that, compared with the ascites carcinoma model group, the body weight gain of the ascites carcinoma mice in the high dose inactivated *Enterococcus faecium* administration group was significantly reduced. In the EAC mouse model, the body weight of tumor-bearing mice increases rapidly due to the formation of ascites. However, the present study found that administration of high dose inactivated *Enterococcus faecium* via the tail vein could slow down the growth rate of body weight of the tumor-bearing mice, which is related to the inhibition of ascites production. In addition, compared with the ascites carcinoma model group, the spleen index of the ascites carcinoma mice of the high dose inactivated *Enterococcus faecium* administration groups was extremely significantly increased, and the spleen index of the ascites carcinoma mice of the medium dose inactivated *Enterococcus faecium* administration group was significantly increased. These results indicated that intravenous administration of inactivated *Enterococcus faecium* can enhance the immune function of the ascites carcinoma mice as well.

TABLE 10

Effect of intravenous administration of inactivated *Enterococcus faecium* on body weight gain and spleen index of ascites carcinoma mice

| Group | Dose | Body weight gain (g) | Spleen index (%) |
|---|---|---|---|
| Ascites carcinoma model group | 0 | 5.939 ± 1.803 | 0.167 ± 0.059 |
| Thymopentin group | 0.2 mg/kg | 6.190 ± 2.087 | 0.221 ± 0.036 |
| High dose inactivated *Enterococcus faecium* group | 5× | 3.928 ± 1.176*△△ | 0.464 ± 0.115**△△ |
| Medium dose inactivated *Enterococcus faecium* group | 1× | 6.553 ± 1.847 | 0.247 ± 0.049* |
| Low dose inactivated *Enterococcus faecium* group | 0.2× | 6.433 ± 0.617 | 0.169 ± 0.022 |

Note:
**indicates an extremely significant difference $P < 0.01$ compared with the ascites carcinoma model group, and
*indicates a significant difference $P < 0.05$ compared with the ascites carcinoma model group;
△△indicates an extremely significant difference $P < 0.01$ compared with the thymopentin group, and
△ indicates a significant difference $P < 0.05$ compared with the thymopentin group.

What is claimed is:

1. An injection for enhancing immune function, comprising:
   inactivated lactic acid bacteria as a main ingredient of the injection;
   wherein, after Gram staining of the inactivated lactic acid bacteria, the inactivated lactic acid bacteria maintain intact bacterial morphology as observed under an oil immersion lens; a number of intact cells of the inactivated lactic acid bacteria per milliliter of the injection is $10^5$ -$10^{12}$; the inactivated lactic acid bacteria is prepared by inactivating lactic acid bacteria; and the lactic acid bacteria are selected from the group consisting of genus *Lactobacillus*, genus *Enterococcus*, genus *Bifidobacterium*, genus *Leuconostoc*, and genus *Streptococcus*;
   wherein the lactic acid bacteria from the genus *Lactobacillus* are *Lactobacillus plantarum* subsp. *Plantarum* or *Lactobacillus brevis*,
   the injection is an intravenous injection.

2. The injection according to claim 1, wherein the lactic acid bacteria are one or more species selected from the group consisting of: *Enterococcus faecium, Lactobacillus plantarum* subsp. *Plantarum, Bifidobacterium longum*, and *Lactobacillus brevis*.

3. The injection according to claim 1, wherein an inactivation method of the lactic acid bacteria is one method selected from the group consisting of a high temperature inactivation, a high temperature and high-pressure inactivation, an ultraviolet inactivation, a chemical inactivation, and a radiation inactivation.

4. The injection according to claim 1, further comprising a pharmaceutically acceptable adjuvant, and the adjuvant contains sufficient salt or monosaccharide to ensure that a suspension solution of the injection has a same or similar osmotic pressure as blood.

5. The injection according to claim 1, wherein the injection is prepared into a powder injection by spray drying or freeze drying; and the powder injection is prepared into a suspension solution during administration.

6. A method for preparing the injection of claim 1, comprising the following steps: after culturing lactic acid bacteria in a conventional liquid medium for 12-36 h, centrifugating at 3000-5000 rpm and retaining a precipitate; after washing the precipitate sufficiently, preparing the precipitate into a suspension solution with a desire concentration;
   and inactivating the suspension solution for 15-30 min under a temperature of 120-122° C. and a pressure of 0.1-0.2 MPa to obtain an inactivated lactic acid bacteria injection.

7. A method of preparing a medicament for enhancing immune function, comprising the step of using the injection of claim 1 as an essential ingredient of the medicament; wherein, the inactivated lactic acid bacteria are single species or a mixture of at least two species of inactivated lactic acid bacteria.

8. The method according to claim 7, wherein the inactivated lactic acid bacteria are obtained by any one inactivation method of high temperature and high-pressure inactivation, ultraviolet inactivation, chemical inactivation, and radiation inactivation.

9. The method according to claim 7, wherein the injection further comprises a pharmaceutically acceptable adjuvant, and the adjuvant contains sufficient salt or monosaccharide to ensure that a suspension solution of the injection has a same or similar osmotic pressure as blood.

10. The method according to claim 7, wherein the injection is prepared into a powder injection by spray drying or freeze drying; and the powder injection is prepared into a suspension solution during administration.

11. The method according to claim 7, wherein the injection is prepared according to the following step: after culturing lactic acid bacteria in a conventional liquid medium for 12-36 h, centrifugating at 3000-5000 rpm and retaining a precipitate; after washing the precipitate sufficiently, preparing the precipitate into a suspension solution with a desire concentration; and inactivating the suspension solution for 15-30 min under a temperature of 120-122° C. and a pressure of 0.1-0.2 MPa to obtain an inactivated lactic acid bacteria injection.

12. The method according to claim 7, wherein the lactic acid bacteria are one or more species selected from the group consisting of: *Enterococcus faecium, Lactobacillus plantarum* subsp. *Plantarum, Bifidobacterium longum*, and *Lactobacillus brevis*.

13. The method according to claim 12, wherein an inactivation method of the lactic acid bacteria is one method selected from the group consisting of a high temperature inactivation, a high temperature and high-pressure inactivation, an ultraviolet inactivation, a chemical inactivation, and a radiation inactivation.

14. The method according to claim 12, wherein the injection further comprises a pharmaceutically acceptable adjuvant, and the adjuvant contains sufficient salt or monosaccharide to ensure that a suspension solution of the injection has a same or similar osmotic pressure as blood.

15. The method according to claim 12, wherein the injection is prepared into a powder injection by spray drying or freeze drying; and the powder injection is prepared into a suspension solution during administration.

16. The method according to claim 12, further comprising the following steps for preparing the injection: after culturing lactic acid bacteria in a conventional liquid medium for 12-36 h, centrifugating at 3000-5000 rpm and retaining a precipitate; after washing the precipitate sufficiently, preparing the precipitate into a suspension solution with a desire concentration; inactivating the suspension solution for 15-30 min under a temperature of 120-122° C. and a pressure of 0.1-0.2 MPa to obtain an inactivated lactic acid bacteria injection.

17. The method according to claim 6, wherein the lactic acid bacteria are one or more species selected from the group consisting of: *Enterococcus faecium, Lactobacillus plantarum* subsp. *Plantarum, Bifidobacterium longum*, and *Lactobacillus brevis*.

18. The method according to claim 6, wherein an inactivation method of the lactic acid bacteria is one method selected from the group consisting of a high temperature inactivation, a high temperature and high-pressure inactivation, an ultraviolet inactivation, a chemical inactivation, and a radiation inactivation.

19. The method according to claim 6, further comprising a pharmaceutically acceptable adjuvant, and the adjuvant contains sufficient salt or monosaccharide to ensure that a suspension solution of the injection has a same or similar osmotic pressure as blood.

* * * * *